(12) United States Patent
Kaneko et al.

(10) Patent No.: US 8,378,091 B2
(45) Date of Patent: Feb. 19, 2013

(54) CELLULOSE DERIVATIVE

(75) Inventors: Hiroaki Kaneko, Hino (JP); Eiichi Kitazono, Hino (JP); Masaya Ito, Hino (JP); Yoshihiko Sumi, Hino (JP)

(73) Assignee: Teijin Limited, Osaka (JP)

( * ) Notice: Subject to any disclaimer, the term of this patent is extended or adjusted under 35 U.S.C. 154(b) by 1039 days.

(21) Appl. No.: 11/997,830

(22) PCT Filed: Aug. 3, 2006

(86) PCT No.: PCT/JP2006/315780
§ 371 (c)(1),
(2), (4) Date: Feb. 4, 2008

(87) PCT Pub. No.: WO2007/015579
PCT Pub. Date: Feb. 8, 2007

(65) Prior Publication Data
US 2010/0279982 A1    Nov. 4, 2010

(30) Foreign Application Priority Data

Aug. 4, 2005 (JP) ................. 2005-226545
Dec. 2, 2005 (JP) ................. 2005-349144

(51) Int. Cl.
C08B 7/00 (2006.01)
C07H 1/00 (2006.01)

(52) U.S. Cl. ............ 536/62; 536/56; 536/63; 536/76; 536/101; 536/124; 514/54; 514/57

(58) Field of Classification Search ........ 536/30, 536/34, 56, 62, 63, 76, 101, 124; 514/54, 514/57
See application file for complete search history.

(56) References Cited

U.S. PATENT DOCUMENTS

| | | | |
|---|---|---|---|
| 4,582,865 A | 4/1986 | Balazs et al. | |
| 4,605,691 A | 8/1986 | Balazs et al. | |
| 5,064,817 A | 11/1991 | Yedgar et al. | |
| 5,906,997 A | 5/1999 | Schwartz et al. | |
| 6,017,301 A | 1/2000 | Schwartz et al. | |
| 6,034,140 A | 3/2000 | Schwartz et al. | |
| 2002/0049183 A1* | 4/2002 | Yedgar et al. ........ | 514/54 |
| 2004/0087492 A1 | 5/2004 | Yedgar et al. | |

FOREIGN PATENT DOCUMENTS

| | | |
|---|---|---|
| EP | 1 228 771 A1 | 8/2002 |
| EP | 1 640 026 A1 | 3/2006 |
| GB | 2 151 244 A | 7/1985 |
| JP | 60-130601 A | 7/1985 |
| JP | 63-37143 A | 2/1988 |
| JP | 1-301624 A | 12/1989 |
| JP | 2-70703 A | 3/1990 |
| JP | 5-508161 A | 11/1993 |
| JP | 6-508169 A | 9/1994 |
| JP | 7-97401 A | 4/1995 |
| JP | 9-296005 A | 11/1997 |
| JP | 10-251447 A | 9/1998 |
| JP | 2003-62057 A | 3/2003 |
| JP | 2003-518167 A | 6/2003 |
| JP | 2004-18841 A | 1/2004 |
| JP | 2004-51531 A | 2/2004 |
| JP | 2004-107503 A | 4/2004 |
| JP | 2005005113 A * | 1/2005 |
| JP | 2005-508827 A | 4/2005 |
| WO | 92/00105 A1 | 1/1992 |
| WO | 92/20349 A1 | 11/1992 |
| WO | 01/34214 A1 | 5/2001 |
| WO | 01/46265 A1 | 6/2001 |
| WO | 2005/000374 A1 | 1/2005 |

OTHER PUBLICATIONS

Charlotte K. Ryan, and Harry C. Sax; Evaluation of a Carboxymethylcellulose Sponge for Prevention of Postoperative Adhesions; The American Journal of Surgery, vol. 169, Jan. 1995, pp. 154-160.

Michael P. Diamond; Reduction of adhesions after uterine myomectomy by Seprafilm membrane (HAL-F): a blinded, prospective, randomized, multicenter clinical study; Fertility and Sterility, vol. 66, No. 6, Dec. 1996, pp. 904-910.

(Continued)

*Primary Examiner* — Shaojia Anna Jiang
*Assistant Examiner* — Everett White
(74) *Attorney, Agent, or Firm* — Sughrue Mion, PLLC (57) ABSTRACT

A cellulose derivative which has a suitable elastic modulus and viscosity when it is dissolved in water and is useful as an adhesion barrier.

The cellulose derivative has a molecular weight of $5 \times 10^3$ to $5 \times 10^6$ and is composed of a repeating unit represented by the following formula (1):

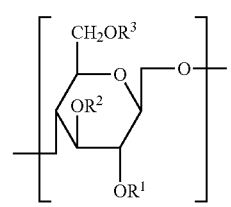

(1)

wherein $R^1$, $R^2$ and $R^3$ are each independently selected from the group consisting of the following formulas (a), (b), (c) and (d) in predetermined amount:

—H    (a)

—$CH_2$—COOH    (b)

—$CH_2$—COOX    (c)

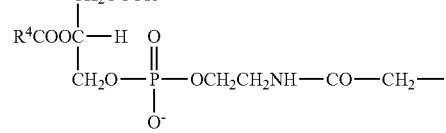

(d)

(X in the formula (c) is an alkali metal, and $R^4$ and $R^5$ in the formula (d) are each independently an alkyl group or alkenyl group having 10 to 28 carbon atoms).

14 Claims, 2 Drawing Sheets

OTHER PUBLICATIONS

James M. Becker, Merril T. Dayton, Victor W. Fazio, David E. Beck, Steven J. Stryker, Steven D. Wexner, Bruce G. Wolff, Patricia L. Roberts, Lee E. Smith, Sharon A. Sweeney, and Marcia Moore; Prevention of Postoperative Abdominal Adhesions by a Sodium Hyaluronated-based Bioresorbable Membrane: A Prosepective, Randomized, Double-blind Multicenter Study; Journal of the American College of Surgeons, Oct. 1996, vol. 183, No. 4, pp. 297-306.

European Search Report dated Oct. 6, 2011 in corresponding European Application No. 06768443.

Phyllis Dan et al. Inhibition of Type I and Type II Phospholipase A2 by Phosphatidyl-Ethanolamine Linked to Polymeric Carriers +, Biochemistry, vol. 37, No. 17, Apr. 1, 1998, pp. 6199-6204.

Sadana J C et al. Endo-(1-4)-beta-d-glucanases from sclerotium rolfsii. Purification, substrate specificity, and mode of action. Carbohydrate Research, Pergamon, GB, vol. 133, No. 2, Oct. 15, 1984.

Kagaku-Daijiten 8 Syukusatsu-ban; Kyoritsu Shuppan Co., Ltd., Feb. 15, 1987, p. 666.

* cited by examiner

CELLULOSE DERIVATIVE

TECHNICAL FIELD

The present invention relates to a cellulose derivative, a manufacturing method thereof and an adhesion barrier.

BACKGROUND ART

The adhesion of a living tissue occurs through its bonding to another tissue when the surface of a damaged organ is regenerated. Therefore, various adhesion barriers comprising a polysaccharide such as cellulose which is a biocompatible material are proposed to prevent adhesion after an operation.

For example, an adhesion barrier which is an aqueous solution of carboxymethyl cellulose is proposed (Am J Surg. 169, 154-159 (1995)). However, this adhesion barrier cannot exhibit an adhesion inhibition effect to the full due to its low retention properties in vivo.

Therefore, many attempts are being made to modify a polysaccharide by various methods or make it water-insoluble.

For example, adhesion barriers prepared by modifying hyaluronic acid and carboxymethyl cellulose with carbodiimide are proposed (JP-A 5-508161, JP-A 6-508169, Fertil Steril. 66. 904-910 (1996), J Am Coll Surg. 183, 297-306 (1996)). An adhesion barrier comprising a cellulose derivative obtained by substituting the hydrogen atom of cellulose with a specific substituent is further proposed (JP-A 1-301624). It is also proposed to use a composite material of carboxymethyl cellulose and a polyether as an adhesion barrier (U.S. Pat. Nos. 5,906,997, 6,017,301, 6,034,140). It is further proposed to use a cellulose derivative prepared by making soluble cellulose hardly soluble in water through an acid treatment as an adhesion barrier (WO01/34214 pamphlet). JP-A 2004-51531 proposes an adhesion barrier containing carboxymethyl cellulose which had been made hardly soluble in water. The adhesion barrier is substantially in a sponge or film form.

U.S. Pat. No. 5,064,817 discloses a reaction for obtaining a phospholipase A2 inhibitor composition by reacting carboxymethyl cellulose having a low molecular weight and phosphatidylethanolamine in a water solvent.

Not relating to an adhesion barrier, as means of chemically crosslinking a polysaccharide, it is proposed that carboxymethyl cellulose should be crosslinked by glyoxal (JP-A 10-251447). Further, a composition prepared by mixing carboxymethyl cellulose with a polyvalent metal ion is proposed (JP-A 63-37143). It is also proposed that hyaluronic acid should be crosslinked by bisepoxide (JP-A 7-97401). It is further proposed that hyaluronic acid should be crosslinked by divinyl sulfone (U.S. Pat. Nos. 4,582,865, 4,605,691). It is further proposed that hyaluronic acid should be crosslinked by formaldehyde or divinyl sulfone (JP-A 60-130601). JP-A 2003-518167 discloses a water-insoluble biocompatible gel prepared by reacting a polyanionic polysaccharide with an activator in an aqueous solution containing a water-compatible organic solvent and gives carboxymethyl cellulose as an example of the polyanionic polysaccharide.

All of the above proposals still have room to study as for adhesion preventing effect, handling properties and safety.

DISCLOSURE OF THE INVENTION

It is an object of the present invention to provide a cellulose derivative which is useful as an adhesion barrier. It is another object of the present invention to provide a cellulose derivative which has a suitable elastic modulus and viscosity and is useful as an adhesion barrier, when it forms a gel. It is still another object of the present invention to provide a gelled adhesion barrier which has excellent retention properties in vivo. It is a further object of the present invention to provide an adhesion barrier which has excellent handling properties. It is a still further object of the present invention to provide a method of manufacturing the cellulose derivative.

The inventors of the present invention have conducted intensive studies to improve an adhesion preventing effect by modifying cellulose with a material having excellent safety to increase its viscosity so as to improve its retention properties in vivo. As a result, the inventors of the present invention have found that a cellulose derivative having a suitable elastic modulus and viscosity and useful as an adhesion barrier can be obtained by substituting the carboxyl group of carboxymethyl cellulose with phosphatidyl ethanolamine which is a substance derived from a living body. The present invention has been accomplished based on this finding.

That is, the present invention is a cellulose derivative having a molecular weight of $5\times10^3$ to $5\times10^6$ and comprising a repeating unit represented by the following formula (1):

wherein $R^1$, $R^2$ and $R^3$ are each independently selected from the group consisting of the following formulas (a), (b), (c) and (d):

(X in the formula (c) is an alkali metal, and $R^4$ and $R^5$ in the formula (d) are each independently an alkyl group or alkenyl group having 10 to 28 carbon atoms, with the proviso that when the equivalents of (a), (b), (c) and (d) are represented by E (a), E(b), E(c) and E(d), respectively, E(b)+E(c)+E(d)=0.3 to 3 and E(d)/{E(b)+E(c)+E(d)}=0.001 to 1).

Further, the present invention is a method of manufacturing a cellulose derivative, comprising the steps of:

dissolving (i) carboxymethyl cellulose having a molecular weight of $5\times10^3$ to $5\times10^6$ and comprising a repeating unit represented by the following formula (1-a):

wherein $R^1$, $R^2$ and $R^3$ are each independently selected from the following formulas (a), (b) and (c):

—H    (a)

—CH$_2$—COOH    (b)

—CH$_2$—COOX    (c)

(X in the formula (c) is an alkali metal, when the equivalents of (a), (b) and (c) are represented by E(a), E(b) and E(c), respectively, E(b)+E(c)=0.3 to 3)
and phosphatidyl ethanolamine represented by the following formula (2):

wherein $R^4$ and $R^5$ are each independently an alkyl group or alkenyl group having 10 to 28 carbon atoms,
in (ii) a ratio that the amount of the phosphatidyl ethanolamine represented by the formula (2) becomes 0.1 to 100 equivalents based on 100 equivalents of the total of E(b)+E(c) of the carboxymethyl cellulose represented by the formula (1-a)
in (iii) a mixed solvent of water and an organic solvent, having a water content of 20 to 70 vol %; and
reacting them in the presence of a catalyst.

The present invention includes an adhesion barrier containing the above cellulose derivative.

BEST MODE FOR CARRYING OUT THE INVENTION

<Cellulose Derivative>

The present invention is a cellulose derivative having a molecular weight of $5\times10^3$ to $5\times10^6$ and composed of a repeating unit represented by the following formula (1).

[Formula (1) structure as shown, same as (1-a) with additional substituent option]

In the formula (1), $R^1$, $R^2$ and $R^3$ are each independently selected from the group consisting of the following formulas (a), (b), (c) and (d).

—H    (a)

—CH$_2$—COOH    (b)

—CH$_2$—COOX    (c)

[structure (d)]
$$R^4COOC-H\;O$$
$$CH_2OCOR^5$$
$$CH_2O-P-OCH_2CH_2NH-CO-CH_2-$$
$$O^-$$

In the formula (c), X is an alkali metal. Examples of the alkali metal include sodium, potassium and lithium.

In the formula (d), $R^4$ and $R^5$ are each independently an alkyl group or alkenyl group having 10 to 28 carbon atoms. Both $R^4$ and $R^5$ are preferably an alkenyl group having 10 to 20 carbon atoms. Both $R^4$ and $R^5$ are more preferably an oleyl group.

When the equivalents of (a), (b), (c) and (d) are represented by E(a), E(b), E(c) and E(d), respectively, the total of E(a), E(b), E(c) and E(d) is 3. The total of E(b), E(c) and E(d) is 0.3 to 3, preferably 0.5 to 2, more preferably 0.6 to 1.5. That is, the total of E(b), E(c) and E(d) is the number of substituents represented by the formulas (b), (c) and (d) when the total number of the substituents $R^1$, $R^2$ and $R^3$ in the repeating unit of the cellulose represented by the formula (1) is 3 equivalents. The ratio of E(b) and E(c) is not particularly limited.

E(d)/{E(b)+E(c)+E(d)} is 0.001 to 1, preferably 0.01 to 1.
E(d)/{E(b)+E(c)} is preferably 0.01 to 1, more preferably 0.1 to 1.

By controlling the amount of the introduced substituent derived from the phosphatidyl ethanolamine represented by the formula (d), the form of the cellulose derivative can be made gelled or solid. For instance, when E(d)/{E(b)+E(c)} is 0.01 to 1 equivalent, the cellulose derivative forms a gel and when it is more than 1 equivalent, the hydrophobic nature of the cellulose derivative becomes high, insoluble matter is produced, a gel is hardly formed, and the cellulose derivative becomes solid.

By controlling the amount of the introduced group of the formula (d), the viscoelasticity and retention properties of the obtained gelled or solid cellulose derivative can be changed. For example, as the amount of the group of the formula (d) introduced into the carboxymethyl cellulose increases, a gel having higher viscosity and elastic modulus is obtained and a gel and a solid having higher retention properties are obtained.

The weight average molecular weight of the cellulose derivative is $5\times10^3$ to $5\times10^6$, preferably $5\times10^4$ to $5\times10^6$, more preferably $5×10^4$ to $1×10^6$. The weight average molecular weight of the cellulose derivative increases because the groups of the formulas (b) and (c) in the carboxymethyl cellulose represented by the following formula (1-a) is substituted by the group represented by the formula (d). That is, the molecular weight increases from that of the carboxymethyl cellulose before the reaction by the modification of the phosphatidyl ethanolamine represented by the formula (2).

<Method of Manufacturing Cellulose Derivative>

The cellulose derivative can be manufactured by dissolving (i) components (X) and (Y) in (ii) a ratio that the amount of the component (Y) becomes 0.1 to 100 equivalents based on 100 equivalents of the total of E(b) and E(c) of the component (X) in (iii) a mixed solvent of water and an organic solvent, having a water content of 20 to 70 vol %, and reacting them in the presence of a catalyst.

(Component (X))

The component (X) is carboxymethyl cellulose having a molecular weight of $5×10^3$ to $5×10^6$ and composed of a repeating unit represented by the following formula (1-a).

(1-a)

In the formula (1-a), $R^1$, $R^2$ and $R^3$ are each independently selected from the following formulas (a), (b) and (c).

(a)

(b)

(c)

In the formula (c), X is an alkali metal. Examples of the alkali metal include sodium, potassium and lithium.

When the equivalents of (a), (b) and (c) are represented by E (a), E (b) and E (c), respectively, the total of E (a), E (b) and E(c) is 3. The total of E(b) and E(c) is 0.3 to 3, preferably 0.5 to 1.5, more preferably 0.6 to 1.0. That is, the total of E(b) and E(c) is the number of substituents represented by the formulas (b) and (c) when the total number of the substituents $R^1$, $R^2$ and $R^3$ in the component (X) is 3.

The weight average molecular weight of the component (X) is $5×10^3$ to $5×10^6$, preferably $5×10^4$ to $5×10^6$, more preferably $5×10^4$ to $1×10^6$.

The component (X) can be manufactured by dissolving pulp (cellulose) in a sodium hydroxide solution, etherifying it with monochloroacetic acid (or a sodium salt) and purifying it.

The structural formula of the preferred carboxymethyl cellulose is the following formula (3) below, and the substitution position of the carboxymethyl group in the cellulose skeleton is preferably the C-6 position.

(3)

(Component (Y))

The component (Y) is phosphatidyl ethanolamine represented by the following formula (2).

(2)

In the formula (2), $R^4$ and $R^5$ are each independently an alkyl group or alkenyl group having 10 to 28 carbon atoms. Both $R^4$ and $R^5$ are preferably an alkenyl group having 10 to 20 carbon atoms. Both $R^4$ and $R^5$ are more preferably an oleyl group.

The component (Y) extracted from an animal tissue or synthesized may be used. Examples of the phosphatidyl ethanolamine include dilauroyl phosphatidyl ethanolamine, dimyristoyl phosphatidyl ethanolamine, dipalmitoyl phosphatidyl ethanolamine, distearoyl phosphatidyl ethanolamine, diarachidoyl phosphatidyl ethanolamine, dibehenoyl phosphatidyl ethanolamine, dilignoceroyl phosphatidyl ethanolamine, dicerotoyl phosphatidyl ethanolamine, dimontanoyl phosphatidyl ethanolamine, dilauroleoyl phosphatidyl ethanolamine, dimyristoleoyl phosphatidyl ethanolamine, dipalmitoleoyl phosphatidyl ethanolamine, dioleoyl phosphatidyl ethanolamine, dinervonoyl phosphatidyl ethanolamine, dilinoleoyl phosphatidyl ethanolamine, dilinolenoyl phosphatidyl ethanolamine, dihiragonoyl phosphatidyl ethanolamine, diarachidonoyl phosphatidyl ethanolamine and didocosahexaenoyl phosphatidyl ethanolamine. Out of these, dioleoyl phosphatidyl ethanolamine is particularly preferred from the viewpoint of solubility in an organic solvent which is used for synthesis.

The phosphatidyl ethanolamine is a safe substance derived from a living body and can enhance hydrophobic nature interaction between the molecules of a cellulose derivative. Therefore, the cellulose derivative of the present invention becomes a hydrogel or a water-insoluble molded product due to the hydrophobic interaction.

(Reaction)

The component (X) and the component (Y) are reacted with each other in a ratio that the amount of the component (Y) becomes 0.1 to 100 equivalents, preferably 5 to 60 equivalents, more preferably 10 to 50 equivalents based on 100 equivalents of the total of E (b) and E (c) of the component (x). When the amount of the component (Y) is smaller than 0.1 equivalent, the formed cellulose derivative does not form a hydrogel. When the amount is larger than 100 equivalents, the hydrophobic nature of the formed cellulose derivative becomes high, insoluble matter is produced, a hydrogel is hardly formed, and the obtained cellulose derivative shows insolubility in an aqueous medium.

The components (X) and (Y) are dissolved in a mixed solvent of water and an organic solvent, having a water content of 20 to 70 vol %, and reacted with each other in the presence of a catalyst.

The catalyst is preferably a carboxyl group activator or a coupling agent. Examples of the catalyst include N-hydroxysuccinimide, p-nitrophenol, N-hydroxybenzotriazole, N-hydroxypiperidine, N-hydroxysuccinamide and 2,4,5-trichlorophenol. Examples of the coupling agent include 1-ethyl-3-(dimethylaminopropyl)-carbodiimide and hydrochloride salts thereof, and dicyclohexylcarbodiimide.

The mixed solvent consists of water and an organic solvent and has a water content of 20 to 70 vol %. When the water content is lower than 20 vol %, the carboxymethyl cellulose does not dissolve in the mixed solvent and when the water content is higher than 70 vol %, the phosphatidyl ethanolamine does not dissolve in the mixed solvent, whereby the reaction does not proceed. The water content is preferably 30 to 60 vol %.

Examples of the organic solvent include tetrahydrofuran, 1,4-dioxane, 1,3-dioxane, 1,3-dioxolan, morpholine, dimethyl sulfoxide, dimethyl acetamide, dimethyl formamide, methanol, ethanol, ethylene glycol, glycerin, diethylene glycol, triethylene glycol, N-methyl-2-pyrrolidone, pyridine, piperidine, piperazine and phenol. The organic solvent is preferably a cyclic ether and particularly preferably at least one selected from the group consisting of tetrahydrofuran, dioxane and dioxolan. Examples of the dioxane include 1,4-dioxane and 1,3-dioxane. Examples of the dioxolan include 1,3-dioxolan.

The reaction temperature is preferably 0 to 60° C. To suppress the formation of a by-product, the reaction is preferably carried out at 0 to 10° C. The reaction environment is preferably a weak acidic environment. It is more preferably at a pH of 6 to 7.

<Gelled Adhesion Barrier>

The adhesion barrier of the present invention contains a cellulose derivative represented by the formula (1).

The gelled adhesion barrier of the present invention is a hydrogel which contains 0.1 to 5.0 parts by weight, preferably 0.3 to 2.0 parts by weight, more preferably 0.5 to 1.5 parts by weight of the cellulose derivative represented by the formula (1) based on 100 parts by weight of water.

When $E(d)/\{E(b)+E(c)\}$ is 0.001 to 1 equivalent, the cellulose derivative represented by the formula (1) forms a gel and when $E(d)/\{E(b)+E(c)\}$ is larger than 1 equivalent, the hydrophobic nature of the cellulose derivative becomes high and insoluble matter is produced, thereby making it difficult to form a gel. $E(d)/\{E(b)+E(c)\}$ of the cellulose derivative represented by the formula (1) is preferably 0.01 to 1.

As for the preferred physical properties of the gel, when the content of a polymer in water is 0.1 to 5%, the gel has such viscoelasticity that it does not flow down when a vessel containing the gel is inclined, can be easily deformed when it is touched with an apparatus such as metal spatula and can be easily applied to an affected part.

As for the preferred viscoelasticity of the gel, when the complex elastic modulus of the gel is measured with a viscoelasticity measuring device called rheometer at a polymer concentration in water of 1 wt %, a temperature of 37° C. and an angular velocity of 10 rad/sec, it is preferably 100 dyn/cm$^2$ or more, more preferably 200 dyn/cm$^2$ or more.

As $E(d)/\{E(b)+E(c)\}$ becomes larger, the retention properties of the gel improve, thereby making it possible to exhibit an adhesion preventing effect for a long time. In this respect, $E(d)/\{E(b)+E(c)\}$ is preferably 0.3 or more. That is, $E(d)/\{E(b)+E(c)\}$ of the gelled adhesion barrier of the present invention is preferably 0.3 to 0.8.

It is conceivable that components other than water contained in the adhesion barrier include a coupling agent used as the catalyst, by-products such as urea formed by the predetermined chemical reaction of the condensing agent, a carboxyl group-containing activator, unreacted phosphatidyl ethanolamine, contaminants contained in each stage of the reaction, and ions used for the control of pH. It is preferred that the contents of all of the compounds should be reduced to such low levels that a foreign matter reaction is not perceived when they are introduced into the living body.

<Solid Adhesion Barrier>

When $E(d)/\{E(b)+E(c)\}$ of the cellulose derivative exceeds 0.5, the hydrophobic nature of the cellulose derivative becomes high, insoluble matter is formed, and the cellulose derivative becomes solid. $E(d)/\{E(b)+E(c)\}$ of the solid adhesion barrier of the present invention is preferably more than 1 and 5 or less.

Even when the solid adhesion barrier of the present invention is insoluble in an aqueous medium, if it enters the living body, it can be swollen with a body fluid to change into a gel. The aqueous medium means water, physiological saline, buffer fluid or an aqueous solution containing alcohol. The term "insoluble" means that the cellulose derivative stays in the living body for a certain period of time, dissolves gradually and is adsorbed into the living body in the end.

The solid adhesion barrier can be manufactured by molding the cellulose derivative by a freeze dry, dry film formation, wet film formation, electrostatic spinning, solidification spinning, span bonding, melt blowing or flash spinning method. As for the shape of the solid adhesion barrier, it may be porous like sponge, nonwoven cloth or a film. The solid adhesion barrier may be used as an adhesion barrier for tissues after an operation or skin moisturizing agent.

EXAMPLES

The following examples are provided for the purpose of further illustrating the present invention but are in no way to be taken as limiting.

(1) The materials used in Examples are given below.
(i) CMCNa: carboxymethyl cellulose sodium (manufactured by Sigma Aldrich Co., Ltd., weight average molecular weight of 700,000, substitution degree of 0.9)
(ii) Tetrahydrofuran (manufactured by Wako Pure Chemical Industries, Ltd.)
(iii) 0.1 M HCl (manufactured by Wako Pure Chemical Industries, Ltd.)
(iv) 0.1 M NaOH (manufactured by Wako Pure Chemical Industries, Ltd.)
(v) EDC:
1-ethyl-3-[3-(dimethylamino)propyl]-carbodi-imide.HCl (manufactured by Wako Pure Chemical Industries, Ltd.)
(vi) HOBt.H$_2$O: 1-hydroxybenzotriazole monohydrate (manufactured by Wako Pure Chemical Industries, Ltd.)
(vii) L-α-dioleoylphosphatidylethanolamine (COATSOME ME-8181 manufactured by NOF Corporation)
(viii) Ethanol for sterilization (manufactured by Wako Pure Chemical Industries, Ltd.)
(ix) Pentobarbital sodium (Nembutal injection solution manufactured by Dainippon Pharmaceutical Co., Ltd.)
(x) Isodine disinfectant (manufactured by Meiji Seika Kaisha Ltd.)
(xi) Physiological saline (manufactured by Otsuka Pharmaceutical Co., Ltd.)

(2) measurement of the content of phospholipid in cellulose derivative

The content of phospholipid in the cellulose derivative was obtained by the analysis of the total content of phosphorus by a phosphorus/molybdenum method.

(3) measurement of complex elastic modulus and viscosity coefficient of hydrogel The complex elastic modulus and viscosity coefficient of a hydrogel were measured at 37° C. by using Rheometer RFIII (of TA Instrument Co., Ltd.). The term "complex elastic modulus" means a constant indicating the ratio of stress to distortion of an elastic material.

(4) intraperitoneal adhesion test

Rats of Nippon Charles River Co., Ltd. were used as intraperitoneal adhesion models. The weights of 30 rats were measured on the date of preparing models, and these rats were divided into groups, each having almost the same weight. Intraperitoneal adhesion models were prepared in accordance with the methods (1, 2) of Taparia et al. and Sachdeva et al. [1. S. Taparia, R. Sharma, S, N. Mathur and V. P. Sharma: Asian Med. J. 28. 58-64, 1985, 2. H. S. Sachdeva, L. V. Gutierrez and A. G. Cox: Br. J. Surg., 58, 382-384, 1971]. That is, each of the rats was fixed supine under the intraperitoneal administration of an anesthetic with pentobarbital sodium (30 mg/kg), the hair of the abdominal part was shaved, and the abdominal part was disinfected with ethanol for sterilization. The operation area was disinfected with Isodine, and the abdominal part was cut open 3 to 4 cm along the middle line to expose the cecum. A certain area (1 to 2 cm$^2$) of the exposed cecum was rubbed with sterile gauze until dot hemorrhage started. After the cecum was returned to its original position, the muscle layers of the cut portions were stitched together continuously, and the skin was sutured with 4 to 5 stitches. The wound area was disinfected with Isodine, and the model was returned into a cage. 29 days after the preparation of models, the abdominal parts of the animals were cut open under anesthesia with pentobarbital sodium and the degree of intraperitoneal adhesion was observed with the naked eye and scored based on the following criteria.

(Grades)

grade 0 (score 0): no adhesion was seen grade 1 (score 1): such degree of adhesion that two adhered parts are very thin and can be easily separated from each other grade 2 (score 2): weak adhesion in a narrow range that can stand slight pulling grade 3 (score 3): very strong adhesion, or adhesion is seen at least 2 locations grade 4 (score 4): adhesion is seen at 3 or more locations Example 1

(Cellulose Derivative)

100 mg of CMCNa was dissolved in 20 ml of water, and further 20 ml of tetrahydrofuran was added. 55 mg (0.000074 mol) (20 equivalents based on 100 equivalents of the carboxyl group of CMCNa) of L-a-dioleoylphosphatidylethanolamine, 16 mg (0.000082 mol) of EDC and 12 mg (0.000082 mol) of HOBt.H$_2$O were added to this solution, dissolved in 10 ml of a mixture of tetrahydrofuran and water in a weight ratio of 1/1, added to a reaction system and stirred all night long. After stirring, the resulting reaction solution was purified by dialysis and freeze dried to obtain a cellulose derivative. The formation of the target product was confirmed by $^1$HNMR (JNM-alpha400 of JEOL Ltd.). The content of phosphatide in the obtained cellulose derivative was measured. The charge equivalents and ratio of (b), (c) and (d) are shown in Table 1 and the equivalents of (b), (c) and (d) obtained from the measurement result of the content of phosphatide are shown in Table 2.

(Hydrogel)

Figure 1:
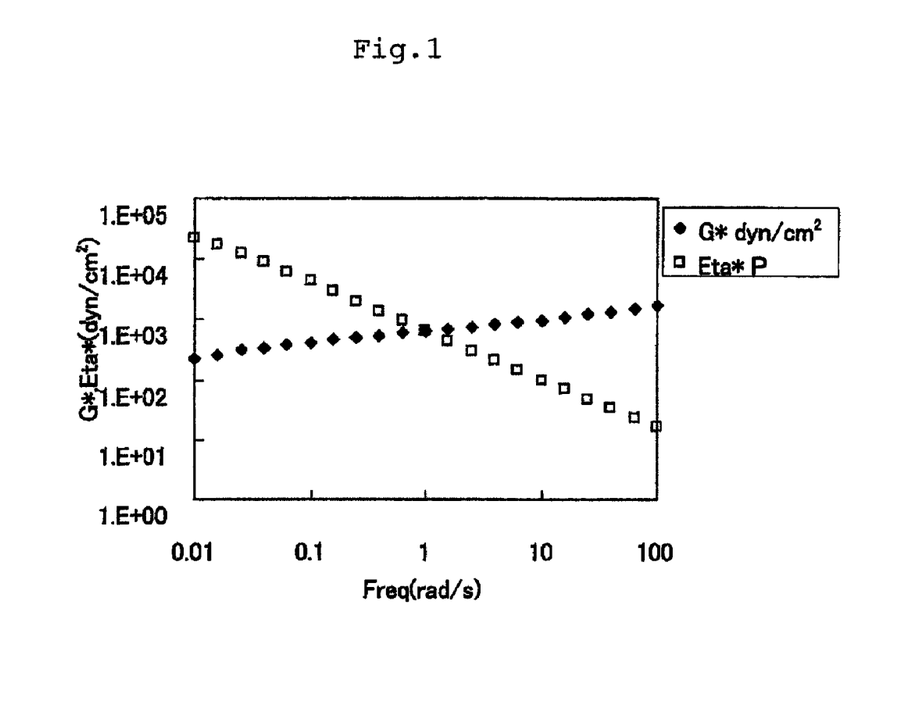
FIG. 1 is a graph showing changes in the complex elastic modulus and viscosity coefficient of a hydrogel of the cellulose derivative of Example 1 by frequency.

10 mg of the free dried cellulose derivative was dissolved in 990 mg of ion exchange water to prepare a hydrogel having a concentration of 1 wt %. The complex elastic modulus and viscosity coefficient of the obtained hydrogel were measured. The results are shown in Table 3 and FIG. 1.

Example 2

(Cellulose Derivative)

A cellulose derivative was obtained in the same manner as in Example 1 except that 111 mg (0.000149 mol) (40 equivalents based on 100 equivalents of the carboxyl group of CMCNa) of L-α-dioleoyl phosphatidyl ethanolamine, 31 mg (0.00016 mol) of EDC and 25 mg (0.00016 mol) of HOBt.H$_2$O were used. The content of phosphatide in the obtained cellulose derivative was measured. The charge equivalents and ratio of (b), (c) and (d) are shown in Table 1 and the equivalents of (b), (c) and (d) obtained from the measurement result of the content of phosphatide are shown in Table 2.

(Hydrogel)

Figure 2:
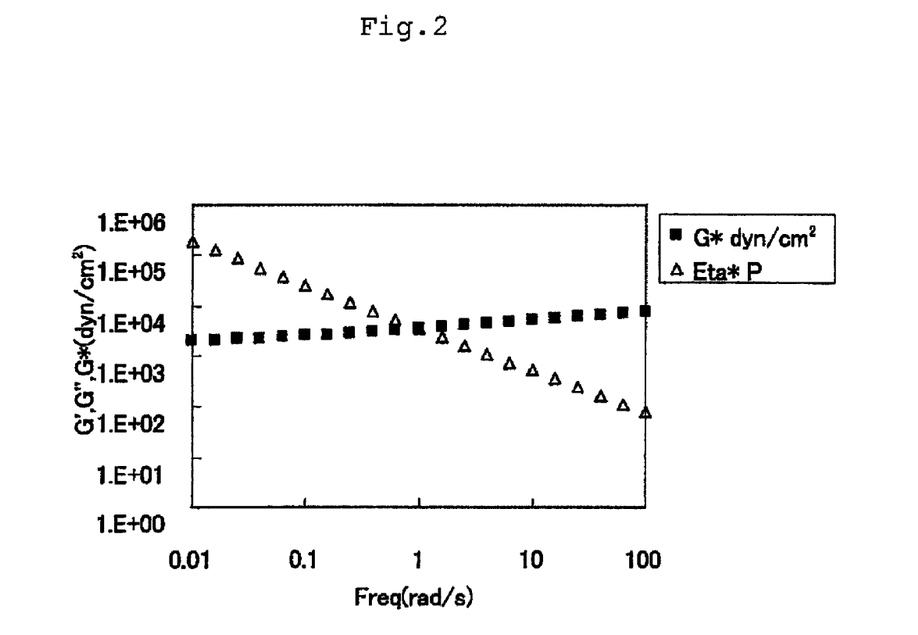
FIG. 2 is a graph showing changes in the complex elastic modulus and viscosity coefficient of a hydrogel of the cellulose derivative of Example 2 by frequency.

A hydrogel was obtained in the same manner as in Example 1. The measurement results of the complex elastic modulus and viscosity coefficient of the obtained hydrogel are shown in Table 3 and FIG. 2.

Example 3

Figure 3:
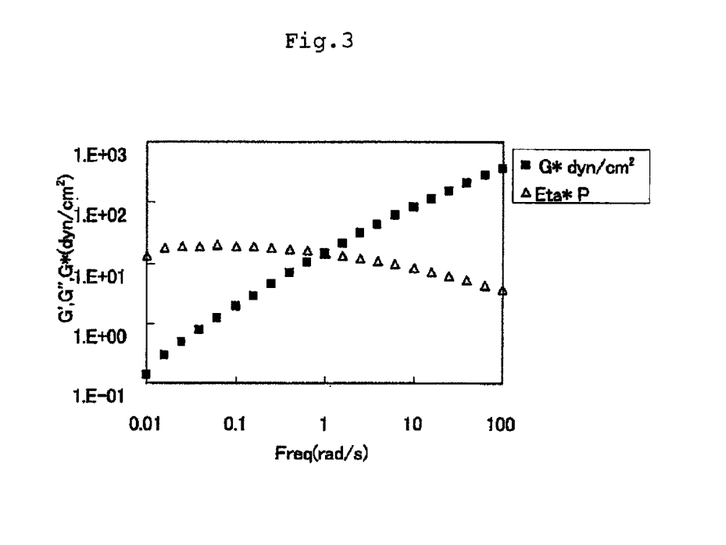
FIG. 3 is a graph showing changes in the complex elastic modulus and viscosity coefficient of a hydrogel of the cellulose derivative of Example 3 by frequency.

A cellulose derivative was obtained in the same manner as in Example 1 except that 222 mg (0.000298 mol) (80 equivalents based on 100 equivalents of the carboxyl group of CMCNa) of L-a-dioleoyl phosphatidyl ethanolamine, 62 mg (0.00032 mol) of EDC and 50 mg (0.00032 mol) of HOBt.H$_2$O were used. The content of phosphatide in the obtained cellulose derivative was measured. The charge equivalents and ratio of (b), (c) and (d) are shown in Table 1 and the equivalents of (b), (c) and (d) obtained from the measurement result of the content of phosphatide are shown in Table 2 and FIG. 3. The obtained cellulose derivative was sponge-like and insoluble in water.

Comparative Example 1

10 mg of CMCNa was dissolved in 990 mg of ion exchange water to measure the viscoelasticity of the resulting product in the same manner as in Example 1. The results are shown in Table 3.

TABLE 1

|  |  | Ex. 1 | Ex. 2 | Ex. 3 | C. Ex. 1 |
|---|---|---|---|---|---|
| E(b) | Equivalent | 0.0 | 0.0 | 0.0 | 0.0 |
| E(c) | Equivalent | 0.72 | 0.54 | 0.18 | 0.9 |
| E(d) | Equivalent | 0.18 | 0.36 | 0.72 | 0.0 |
| E(b) + E(c) + E(d) | Equivalent | 0.9 | 0.9 | 0.9 | 0.9 |
| E(d)/{E(b) + E(c) + E(d)} | — | 0.2 | 0.4 | 0.8 | 0.0 |

Ex.: Example
C. Ex.: Comparative Example

TABLE 2

|  | Ex. 1 | Ex. 2 | Ex. 3 |
|---|---|---|---|
| E(b) | Equivalent | 0.0 | 0.0 | 0.0 |
| E(c) | Equivalent | 0.73 | 0.58 | 0.26 |
| E(d) | Equivalent | 0.17 | 0.32 | 0.64 |
| E(b) + E(c) + E(d) | Equivalent | 0.9 | 0.9 | 0.9 |
| E(d)/{E(b) + E(c) + E(d)} | — | 0.19 | 0.36 | 0.71 |

Ex.: Example
C. Ex.: Comparative Example
E(b): —$CH_2$—COOH
E(c): —$CH_2$—COONa
E(d):

($R^4$ and $R^5$ are oleoyl groups.)

TABLE 3

|  | Complex elastic modulus (dyn/cm$^2$)* | Viscosity coefficient (P)* |
|---|---|---|
| Ex. 1 | 991 | 99 |
| Ex. 2 | 5135 | 513 |
| Ex. 3 | — | — |
| C. Ex. 1 | 83 | 8 |

Ex.: Example
C. Ex.: Comparative Example
*Complex elastic modulus and viscosity coefficient are values at a frequency of 10 rad/s.

Example 4

The ceca of rats as intraperitoneal adhesion models were caused to bleed petechially and returned into their abdominal cavities, and a hydrogel (1 mL) of the cellulose derivative prepared in Example 1 was applied to the abrasion parts of 10 rats. After 29 days, the abdominal parts of the rats were cut open under anesthesia with pentobarbital sodium to check the degree of intraperitoneal adhesion with the naked eye and score it.

Example 5

The procedure of Example 4 was repeated except that a hydrogel (1 mL) of the cellulose derivative prepared in Example 2 was used to check the degree of intraperitoneal adhesion with the naked eye and score it.

Comparative Example 2

The procedure of Example 4 was repeated except that a hydrogel (1 mL) was not applied to the abrasion parts to check the degree of intraperitoneal adhesion with the naked eye and score it.

The intraperitoneal adhesion score of each case was expressed by mean value±standard error (mean±S.E.). A Wilcoxon rank total test was made on the groups of Examples 4 and 5 and Comparative Example 2. The SAS (Trademark Registration) System Release 8.2 (TS2M0) for Windows (of SAS Institute Inc.) was used as statistical software and the EXSAS Version 7.10 (of Arm Co., Ltd.) was used as its cooperative system.

Figure 4:
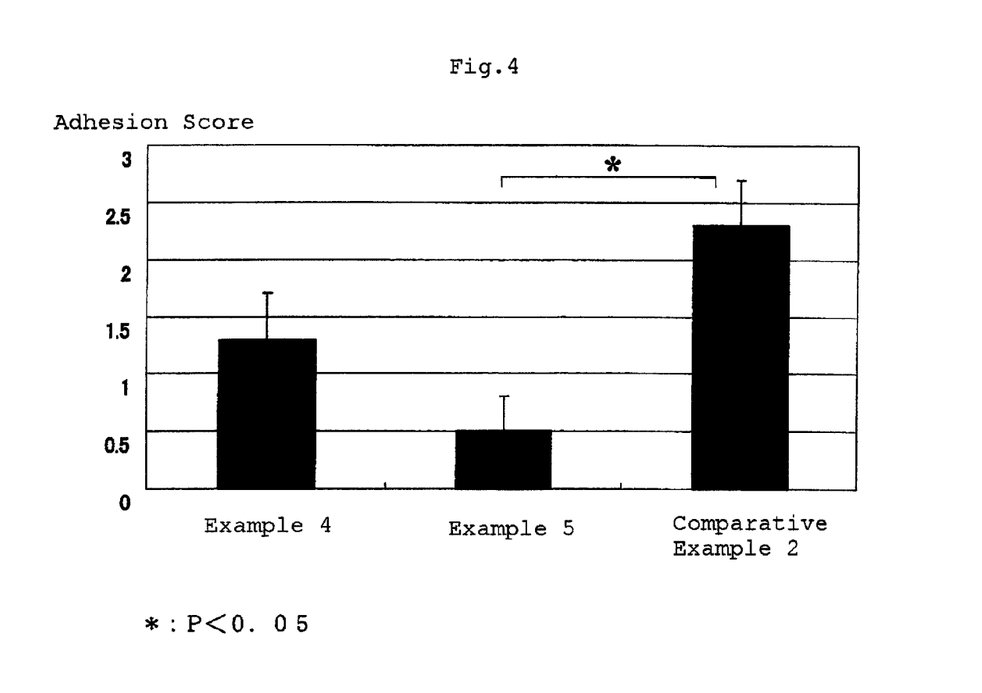
FIG. 4 is a graph showing the adhesion scores of the groups of Examples 4 and 5 and Comparative Example 2.

The effect of each derivative which was applied to the rats as the intraperitoneal adhesion models for 29 days was investigated and the results are shown in FIG. 4.

As shown in FIG. 4, Example 4 shows an adhesion score of 1.3±0.4. Example 5 shows an adhesion score of 0.5±0.3. Meanwhile, Comparative Example 2 shows an adhesion score of 2.3±0.4. Although no statistically significant difference is seen between Example 4 and Comparative Example 2, the adhesion score tends to decrease and the adhesion score of Example 5 is statistically significantly smaller than that of Comparative Example 2 (P<0.05). It is understood from the above results that the derivatives used in Examples 4 and 5 have an adhesion preventing effect when it is applied for 29 days.

Effect of the Invention

When the cellulose derivative of the present invention is dissolved in water, it becomes a gel having a suitable elastic modulus and viscosity which can be used as an adhesion barrier. Since the cellulose derivative of the present invention contains phosphatidyl ethanolamine derived from a living body, it is safe. The adhesion barrier of the present invention has excellent retention properties in vivo and an excellent adhesion preventing effect. According to the manufacturing method of the present invention, the cellulose derivative can be manufactured efficiently. The gelled adhesion barrier of the present invention has sufficiently high softness and viscosity and excellent handling properties, can be applied to a part having a complex shape and can be used in an operation using an endoscope.

Industrial Feasibility

The adhesion barrier of the present invention can be used to prevent the adhesion of the surface of a living tissue which has been damaged during the operation of the spinal cord, joint, sinew or nerve. Stated more specifically, in the case of the operation of the spinal cord, for example, adhesion can be prevented by applying the adhesion barrier of the present invention to separate a dura mater from a part around a nerve root.

When adhesion occurs, the removal of adhesion must be carried out to eliminate pain or ensure an operating region. Adhesion can be prevented by applying the adhesion barrier of the present invention, thereby making it possible to avoid a further operation, improve medical economy and further enhance the quality of life of a patient.

Further, it can be used for hysteromyomectomy using celiotomy or an abdominoscope in the operation of genecology. Adhesion can be prevented by applying the adhesion barrier of the present invention to a wound region after operation.

The adhesion barrier of the present invention has excellent retention stability in vivo and is useful as an adhesion barrier. Especially a gelled adhesion barrier can be applied to a region having a complex shape and can be easily used in an operation using an endoscope.

The invention claimed is:

1. A cellulose derivative having a molecular weight of $5\times10^3$ to $5\times10^6$ Daltons and comprising a repeating unit represented by the following formula (1):

(1)

wherein $R^1$, $R^2$ and $R^3$ are each independently selected from the group consisting of the following formulas (a), (b), (c) and (d):

—H   (a)

—CH$_2$—COOH   (b)

—CH$_2$—COOX   (c)

(d)

(X in the formula (c) is an alkali metal, and $R^4$CO and $R^5$CO in the formula (d) are each an oleoyl group, with the proviso that when the equivalents of (a), (b), (c) and (d) per monosaccharide unit are represented by E(a), E(b), E(c) and E(d), respectively, E(a)+E(b)+E(c)+E(d)=3, E(b)+E(c)+E(d)=0.3 to 3 and E(d)/{E(b)+E(c)+E(d)}=0.001 to 1).

2. The cellulose derivative according to claim 1, wherein E(d)/{E(b)+E(c)+E(d)}=0.01 to 1.

3. The cellulose derivative according to claim 1, wherein E(d)/{E(b)+E(c)} of the cellulose derivative is 0.01 to 1.

4. The cellulose derivative according to claim 1 which has a molecular weight of $5\times10^4$ to $5\times10^6$ Daltons.

5. The cellulose derivative according to claim 1, wherein the formula (d) is derived from L-α-dioleoylphosphatidylethanolamine.

6. An adhesion barrier containing the cellulose derivative of claim 1.

7. The adhesion barrier according to claim 6 which is gelled and contains 0.1 to 5.0 parts by weight of the cellulose derivative based on 100 parts by weight of water.

8. The adhesion barrier according to claim 7, wherein E(d)/{E(b)+E(c)} of the cellulose derivative is 0.01 to 1.

9. The adhesion barrier according to claim 6, wherein E(d)/{E(b)+E(c)} of the cellulose derivative is more than 1 and 5 or less and is solid.

10. A method of manufacturing a cellulose derivative, comprising the steps of:

dissolving (i) carboxymethyl cellulose having a molecular weight of $5\times10^3$ to $5\times10^6$ Daltons and comprising a repeating unit represented by the following formula (I-a):

(I-a)

wherein $R^1$, $R^2$ and $R^3$ are each independently selected from the following formulas (a), (b) and (c):

—H   (a)

—CH$_2$—COOH   (b)

—CH$_2$—COOX   (c)

(X in the formula (c) is an alkali metal, with the proviso that when the equivalents of (a), (b) and (c) are represented by E(a), E(b) and E(c), respectively, E(b)+E(c)=0.3 to 3) and phosphatidyl ethanolamine represented by the following formula (2):

(2)

wherein $R^4$CO and $R^5$CO are each an oleoyl group, in (ii) a ratio that the amount of the phosphatidylethanolamine represented by the formula (2) becomes 0.1 to 100 equivalents based on 100 equivalents of the total of E(b)+E(c) of the carboxymethyl cellulose represented by the formula (I-a)

in (iii) a mixed solvent of water and an organic solvent, having a water content of 20 to 70 vol %; and reacting them in the presence of a catalyst, wherein the catalyst is a carboxyl group activator or a coupling agent.

11. The manufacturing method according to claim 10, wherein the organic solvent is at least one selected from the group consisting of tetrahydrofuran, dioxane and dioxolan.

12. The manufacturing method according to claim 10, wherein the catalyst is a 1-ethyl-3-(dimethylaminopropyl)-carbodiimide hydrochloride salt.

13. The manufacturing method according to claim 10, wherein the reaction is carried out at 0 to 10° C.

14. The method according to claim 10, wherein the phosphatidyl ethanolamine represented by formula (2) is L-α-dioleoylphosphatidylethanolamine.

* * * * *